United States Patent [19]

Coward et al.

[11] 4,376,116

[45] Mar. 8, 1983

[54] POLYAMINE BIOSYNTHESIS INHIBITORS

[75] Inventors: James K. Coward; Kuo-Chang Tang, both of Troy, N.Y.

[73] Assignee: Research Corporation, New York, N.Y.

[21] Appl. No.: 298,325

[22] Filed: Sep. 1, 1981

[51] Int. Cl.³ .................... A61K 31/70; C07H 19/16
[52] U.S. Cl. ...................... 424/180; 536/26; 536/24
[58] Field of Search ................ 536/24, 26; 424/180

[56] References Cited

U.S. PATENT DOCUMENTS 3,954,726  5/1976  Fiecchi ............................ 536/26
4,139,563  2/1979  Metcalf et al. ................... 536/26
4,210,639  7/1980  Chiang et al. ................... 536/26

OTHER PUBLICATIONS

Coward et al., J. Med. Chem., vol. 20, pp. 500–505, 1977.

*Primary Examiner*—Blondel Hazel

*Attorney, Agent, or Firm*—Oblon, Fisher, Spivak, McClelland & Maier

[57] ABSTRACT

A compound having the formula:

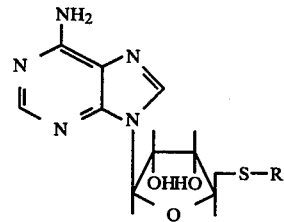

wherein R is

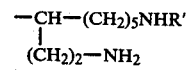

wherein R' is hydrogen or aminopropyl and salts thereof.

4 Claims, No Drawings

POLYAMINE BIOSYNTHESIS INHIBITORS

ACKNOWLEDGEMENT

The invention described herein was made in the course of work under a grant or award from the Department of Health and Human Services.

BACKGROUND OF THE INVENTION

1. Field of the Invention

The present invention relates to polyamine biosynthesis inhibitors. More particularly, the present invention relates to derivatives of S-adenosyl-(1,8-diamino-3-thiooctane) as polyamine biosynthesis inhibitors.

2. Description of the Prior Art

The synthesis of such polyamines as putrescine, spermidine and spermine in biological systems is of considerable importance in cellular replication, as evidenced by the multitude of stimuli which elicit changes in the intracellular level of the polyamines and/or their biosynthetic enzymes. In biological systems the polyamines are synthesized by a pair of aminopropyltransferases (APT), which are spermidine synthase and spermine synthase. In these reactions, nucleophilic attack by either putrescine or spermidine at an electrophilic methylene carbon atom of decarboxylated S-adenosylmethionine (dcSAM) results in the synthesis of the polyamine products, spermidine and spermine, respectively. (U.S. Pat. Nos. 3,954,726 and 4,028,183 describe the preparation of stable salts of S-adenosyl-L-methionine (SAM) which is the parent compound of dcSAM.) A related study in enzyme catalyzed alkylation reactions has shown that the mechanism of reactions involving the S-adenosylmethionine (SAM)-dependent methylase enzyme, catechol-O-methyltransferase (COMT), proceeds by a random, sequential mechanism which involves direct nucleophilic attack of the catechol hydroxyl group on the methyl carbon atom of S-adenosylmethionine. (R. W. Woodard et al, *J. Biol. Chem.*, 255, 9124 (1980)) This mechanism probably involves general-base catalyzed proton abstraction. In another study non-specific inhibition of the enzymatic action of SAM-dependent methylases and aminopropyl transferases by the nucleoside products, S-adenosyl-homocysteine (SAH) and 5'-methylthioadenosine (MTA), respectively. However, a need continues to exist for specific inhibitors of alkyl transfer reactions by a molecule which embodies the structural features of proposed enzyme-bound transition states.

SUMMARY OF THE INVENTION

Accordingly, one object of the present invention is to provide specific inhibitors for enzyme catalyzed alkyl transfer reactions involving the enzymes spermidine synthase and spermine synthase.

Another object of the present invention is to provide a compound useful as an antiparasitic agent and in the treatment of cancer and cystic fibrosis.

Still another object of the present invention is to provide a compound which is useful in the study of polyamine biochemistry.

Accordingly, these objects and other objects of the present invention as hereinafter will become more readily apparent can be attained by a compound having the formula:

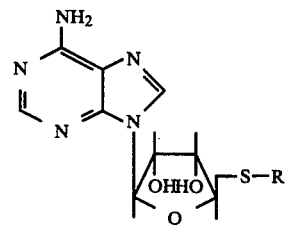

wherein R is

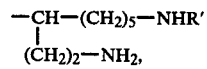

wherein R' is hydrogen or aminopropyl, and the protonated salts thereof.

DETAILED DESCRIPTION OF THE PREFERRED EMBODIMENTS

It is believed that the following structure A is representative of the transition-state of the direct nucleophilic attack by putrescine on the aminopropyl group of decarboxylated S-adenosylmethionine (dcSAM).

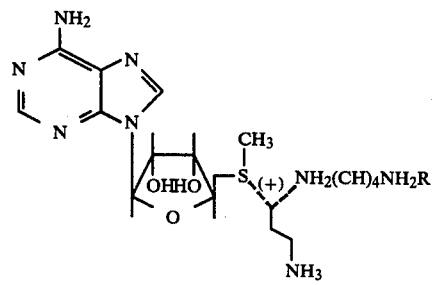

wherein R is hydrogen or aminopropyl.

Based on the hypothetical transition-state shown above, a series of compounds has been postulated as possibly mimicking the hypothetical transition state. These compounds have the formulas:

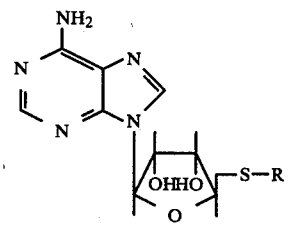

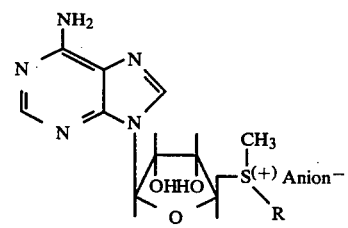

wherein a, R is methyl; b, R is and c, R is

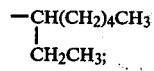

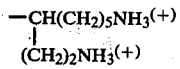

The anion of compound II can be any suitable anion such as perchlorate, $BF_4^-$, or the like.

Compounds I a-c can be prepared by any convenient method. However, they can be readily prepared by coupling 5'-deoxy-5'-chloroadenosine with an appropriate thiol compound. Compounds II a-c can be synthesized by methylation of the corresponding I a-c compounds using a known methylation technique. Each of the compounds was tested for the ability to inhibit purified spermidine synthase obtained from the rat ventral prostate by the procedure detailed by H. Hibasami et al, Biochem. U.J. 187, 419–428 (1980) except that the dcSAM concentration was maintained at 21 μm, and the results are shown in Table 1 below. (In the tests involving MTA phosphorylase, the procedure described by H. Hibasami was employed at a methyl thioadenosine concentration of 100 μm.)

TABLE 1

INHIBITION OF RAT PROSTATE SPERMIDINE SYNTHASE AND METHYLTHIOADENOSINE PHOSPHORYLASE BY 1 AND 2[a]

| Compound | Concentration | Spermidine Synthase | % Inhibition Spermine Synthase | MTA Phosphorylase[d] |
|---|---|---|---|---|
| Ia | 50 | 61 | 80 | Substrate |
|  | 100 | 82 | 98 |  |
| Ib | 25 | 0 | 11 | — |
|  | 100[b] | 0 | 22 | 25 |
| Ic | 10 | 97 | — | 3 |
|  | 25 | 97 | 10 | 8 |
|  | 50 | 99 | — | — |
|  | 100 | 99 | 15 | 10 |
| IIa | 50 | 0 | 68 | — |
|  | 250 | 6 | 82 | 30 |
| IIb | 50 | 7 | 35 | — |
|  | 100 | 14 | 56[c] | 11 |
|  | 250 | 44 | 75 | 21 |
| IIc | 10 | 32 | 7 | — |
|  | 50 | 84 | 40 | — |
|  | 100 | 92 | 59[c] | 16 |
|  | 250 | 96 | 86 | 25 |

[a]Enzyme assays were carried out as described in the text, except that decarboxylated S— adenosylmethionine concentration was 42 μM when assaying 1a with spermidine and spermine synthase.
[b]Concentration range of 1b limited by poor solubility.
[c]A second preparation of spermine synthase was inhibited 19% and 28% by 100 μM 2b and 2c, respectively.
[d]MTA = methylthioadenosine The data in Table 1 clearly delineate the structural requirements which a compound must have for the inhibition of spermidine synthase. The sulfonium salt IIc represents an analog of the transition state in which the full charge is maintained on sulfur and dispersed on nitrogen. On the other hand, the data in the table show that compound Ic, with no charge on sulfur, is a more potent inhibitor of spermidine synthase than the fully charged methyl sulfonium salt IIc. This is a somewhat unexpected result since from consideration of mechanistic studies of model reactions, as well as enzyme-catalyzed methylation reactions, it was anticipated that the charge on sulfur is only partially removed in the transition-state. However, these results are similar to the observed inhibition of many methylases by the thioether product, S-adenosyl-L-homocysteine, as reported by G. L. Cantoni et al in Transmethylation, Elsevier North Holland, 1979 p. 155–164, which has a $K_i$ considerably less than the Km value for the corresponding sulfonium substrate, S-adenosyl-L-methionine. A possible explanation for the superior effectiveness of compound Ic is that charge dispersal at sulfur in transmethylation reactions as would be achieved by compound Ic results in tighter binding by the thioether, compound Ic, than the sulfonium compound IIc. The obtained experimental evidence is also supported by the reported finding that the methyl group of decarboxylated S-adenosyl-L-methionine can be replaced by an ethyl or propyl group and still retain most of the substrate activity. The evidence suggests that the methyl group of decarboxylated S-adenosyl-L-methionine is used simply to produce an electrophilic sulfonium salt which is susceptible to nucleophilic attack by putrescine or spermidine (see the postulated transition state above where R is hydrogen and aminopropyl respectively). The loss of charge at sulfur in the transition state would be facilitated by an active site of low polarity. This fact may be the reason for the large differences in inhibition observed between compounds Ic and IIc.

The observation that the desamine analogs of compounds Ic and IIc, i.e., compounds Ib and IIb, do not at all inhibit the action of spermidine synthase shows that the inhibition observed is dependent on many of the structural features of the above shown transition state wherein R is hydrogen. Moreover, the non-adenosine fragment of compound Ic, i.e., 1,8-diamine-3-octanol, is completely inactive as an inhibitor of either spermidine synthase spermine synthase at concentrations as high as 250 μM. Still further, in further characterizing the inhibiting characteristics of Ic, the $I_{50}$ value of compound Ic is about $4 \times 10^{-7}$ M while the Km literature values for mammalian spermidine synthase are considerably greater, i.e., about $5 \times 10^{-5}$ M and about $2 \times 10^{-4}$ M. However, the $I_{50}$ value for compound Ic is somewhat greater than the product of the two Km values (about $10^{-8}$ M).

The specificity of inhibition characteristics of the present compounds for target enzymes is further demonstrated by the data in Table 1 for compounds I and II with respect to rat prostate spermine synthase. This enzyme catalyzes the synthesis of spermine in the reaction of spermidine with decarboxylated S-adenosylmethionine, presumably by direct nucleophilic attack as shown by the above transition state wherein R is aminopropyl. As shown by the data in Table 1, compounds Ib and Ic exhibit almost no inhibitory activity against spermine synthase, while compounds IIb and IIc exhibit only modest inhibition of the enzyme. The fact that both compounds IIb and IIc inhibit spermine synthase to about the same extent suggests that the action of the enzyme is generally inhibited by sulfonium compounds. This fact has been demonstrated previously with sulfonium compounds such as S-adenosyl-L-methionine. Indeed, the simplest adenosyl sulfonium salt IIa disclosed above shows inhibition of spermine synthase. Accordingly, the data obtained substantiate the unusual inhibitory specificity of compound Ic against spermidine synthase. These data also suggest that compound Ic mimics the transition state shown above where R is hydrogen and not aminopropyl.

It has been demonstrated that compounds Ia is an inhibitor of both spermidine synthase and spermine synthase. Because of this fact, it is important to determine the effect of compounds I and II on the activity of methylthioadenosine phosphorylase since it is conceivable that this enzyme can hydrolyze thioethers of the type of compound I or can be inhibited by sulfonium compounds of the type of compound II. This, in turn, would lead to metabolic degradation of the inhibitors and/or to increased levels of methylthioadenosine in cell culture experiments. However, the data obtained in Table 1 show that neither compound Ic nor IIc has any significant effect on methylthioadenosine phosphorylase. Therefore, it appears that compounds Ic and IIc may be used in biological studies without the concern of metabolic inactivation by this phosphorylase or without concern of affecting spermidine biosynthesis by increasing intracellular levels of the product inhibitor methylthioadenosine.

In the light of the evidence obtained which clearly links the structure of the transition state for spermidine synthesis via spermidine synthase catalysis with the inhibitory characteristics of compound Ic, it is apparent that the structure of the compound I′

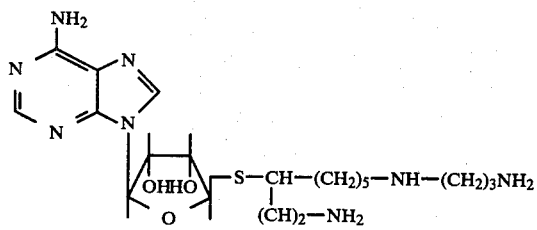

mimics the transition state for spermine synthesis via catalysis with spermine synthase and therefore would be expected to inhibit the action of spermine synthase.

The general synthetic approach to compounds of the type of compounds I and II is shown in Scheme I as follows. These routes are well documented in the literature (see J. K. Coward, *J. Med. Chem.*, 20, 500 (1977) and G. L. Anderson, *J. Med. Chem.*, 24, in press (1981) and K. C. Tang et al, *J. Med. Chem.*, 24, in press (1981)).

SCHEME I

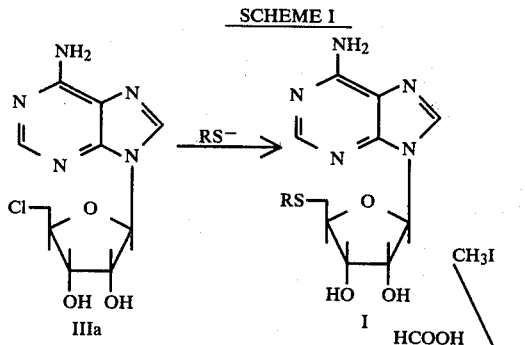

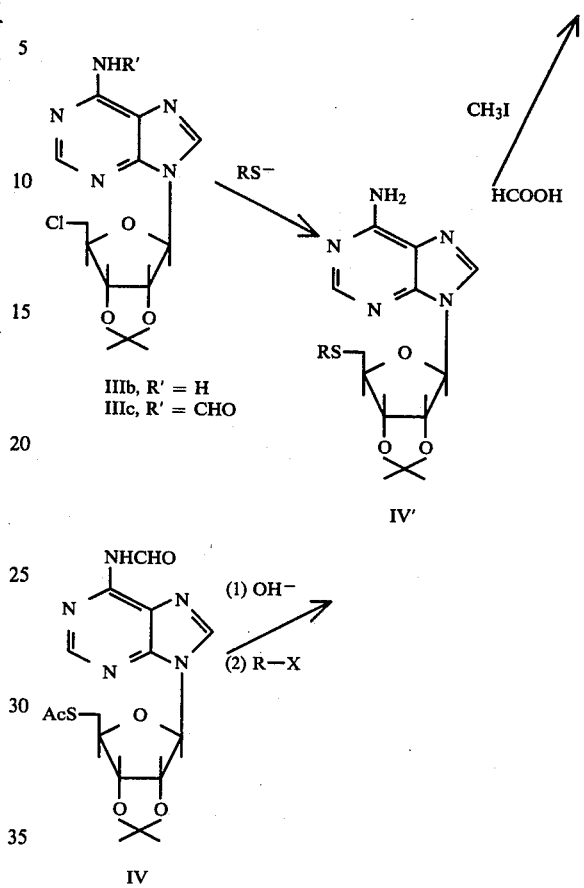

R in formulas I and IV′ can be methyl, 3-octyl or 1,8-diamino-3-octyl

In order to prepare compounds I and II whose properties have been discussed above, it is necessary to react 5′-deoxy-5′-thio- and 5′-deoxy-5′-chloroadenosine with the appropriate alkyl halide and alkylthiol compounds respectively. Compound Ib can be prepared by reacting 5′-deoxy-5′-chloroadenosine with

wherein Ac represents any well known acyl radical such as formyl, acetyl, propionyl, benzoyl or the like. The resulting thioether is then hydrolyzed to form a thiolate anion. This thiolate can then displace chloride ion from the adenosine compound at a noncritical temperature which normally ranges from about ambient to about 60° C. At too high a temperature, disulfide formation will occur. However, this can easily be avoided by decreasing the temperature. The reaction is normally conducted in a polar solvent such as dimethylformamide, dimethylsulfoxide or the like. The acylated thiooctane starting material can, in turn, be prepared by reacting 3-halooctane with a metal (−)SAc compound such as an alkali metal or alkaline earth metal thioacetate, thioformate or the like in a polar solvent such as dimethylformamide, dimethylsulfoxide or the like at a noncritical temperature which is about ambient or a little higher.

By conventional organic synthesis methodology, the 3-halooctane compound can be prepared by converting 3-octanone to 3-octanol and then reacting the 3-octanol with a halogenating agent such as PBr$_3$.

Compound IIb can be prepared from compound Ib by methylation of the same with a methylating reagent such as a methyl halide or dimethylsulfate, although CH$_3$I is preferred in a solvent such as formic acid, acetic acid, or the like. Besides serving as the polar reaction medium, the acid solvent protects the nucleoside by protonation during methylation.

Compound IIb can also be prepared by reacting the 5'-deoxy-5'-thioadenosine derivative generated in situ from IV, via based catalyzed hydrolysis with 3-halooctane under the same conditions described above for the methylation of compound Ib with a methylating agent such as methyliodide.

Compounds Ic and IIc can be prepared by a method which involves the preparation of 1,8-diamino-3-octanol in which the amino groups are protected by t-butoxycarbonyl functionality. Accordingly, protected diaminooctanol is prepared by reaction of 1,8-dihalo-3-octanol with an alkali salt of di-t-butoxycarbonyl imide, i.e., $M^{(+)}$(t-butoxycarbonyl)$_2 N^-$, at a noncritical temperature ranging from about ambient up to about 75° C. in a solvent such as dimethylformamide, dimethylsulfonide or the like. Suitable alkali ions $M^{(+)}$ include the alkali metal ions, alkaline earth metal ions and the like. The protected diamino compound obtained has the formula: (Boc)$_2$NCH$_2$CH$_2$CHOH(CH$_2$)$_4$CH$_2$N(Boc)$_2$. The protected diamino compound can then be converted to the corresponding 3-tosylate compound followed by conversion of the tosylate to the 3-halo derivative by conventional tosylation and halogenation reaction conditions. Having obtained the protected diamino-3-halooctane, the same can be reacted with the 5'-deoxy-5'-thioadenosine derivative generated in situ from compound IV by treatment with a base such as an alkali or alkaline earth metal hydroxide or alkoxide in a polar solvent such an an alcohol, thereby obtaining intermediate IV'. Acid hydrolysis of intermediate IV' results in removal of the ketal group as well as the protecting butoxycarbonyl groups and the synthesis of S-adenosyl-1,8-diaminooctyl compound Ic. If the product desired is the alkyl sulfonium compound IIc, it can be simply obtained by treating intermediate IV' with a methylating agent under acidic conditions as described above. In this reaction the sulfur atom is methylated while the ketal group is cleaved from the adenosine nucleus.

Compound Ic can also be prepared by a route which involves the preparation of an azide intermediate. In this scheme, 1,8-dihalo-3-octanol is converted to the corresponding 1,8-diazido-3-octanol compound by reaction of the dihalooctanol starting compound with an azide salt such as an alkali metal azide, an alkaline earth metal azide or the like in a polar solvent such as dimethylformamide, dimethylsulfoxide or the like. The temperature of this reaction is not critical and the reaction is usually conducted at ambient temperatures. Tosylation of the 1,8-diazido-3-octanol compound under conventional conditions results in the corresponding 1,8-diazido-3-tosyloctane compound. The tosylate can then be converted to the corresponding 1,8-diazido-3-acylthiooctane compound by treatment of the tosylate with a metal $^{(-)}$SAc salt in a polar solvent such as dimethylformamide, dimethylsulfoxide or the like at ambient temperature. Having obtained the 1,8-diazido-3-acylthiooctane compound, the same can be reacted with 5'-deoxy-5'-chloroadenosine in a basic reaction medium which affects the in situ hydrolysis of the acylthiooctane compound to the corresponding 1,8-diazido-3-thiooctanol intermediate which immediately reacts with the chloroadenosine starting material thereby completing the synthesis of the adenosyl derivative whose octyl substituent contains the terminal azido groups. Upon reduction of the azido groups with a conventinal azido reducing agent such as triphenylphosphine/pyridine, the desired diamino thioether Ic is obtained.

The compound of the present invention which mimics the transition state for spermine synthesis identified as compound I' above can be prepared by a synthesis procedure similar to that described above for the preparation of compound Ic wherein haloadenosine is reacted with the thiol compound generated by hydrolysis in situ from the S-acylated precursor of 1,12-diamino-3-thio-9-azadodecane.

In the light of the spermidine synthase inhibiting characteristics of the compound of the present invention, the present compound finds utility as an anti-parasitic agent and is useful in biochemical studies where the inhibition of the activity of spermidine synthase is desired. The properties of the present compound also suggest utility of the same in the treatment of cystic fibrosis and cancer.

The compound of the present invention can be radiolabeled by conventional technology and therefore can be used in systems where the tracing of the inhibitory activity of the compound is desired.

Having generally described this invention, a further understanding can be obtained by reference to certain specific examples which are provided herein for purpose of illustration only and are not intended to be limiting unless otherwise specified.

EXPERIMENTAL SECTION

General: All chemicals were of reagent quality and used without further purification with the following exceptions: pyridine and N,N-dimethylformamide (DMF) were dried over potassium hydroxide pellets and distilled; methyl ketone was distilled over CaSO$_4$ prior to use; dimethyl sulfoxide (DMSO) and hexamethylphosphoric triamide (HMPA) was distilled over calcium hydride prior to use; commercial tosyl chloride was recrystallized from petroleum ether-benzene; thionyl chloride was freshly distilled prior to use, and methanol was kept over molecular sieves (4A). Potassium thioacetate was triturated with dry 2-butanone several times and dried in vacuo. 5'-Deoxy-5'-chloroadenosine was prepared by a modification of known literature procedures. All compounds had spectral properties (nmr, IR, UV) consistent with their assigned structures. All adenosyl sulfonium compounds ($\lambda$max=259 nm) decomposed rapidly in 0.1 N NaOH to give adenine ($\lambda$max=268 nm).

Preparation of compounds Ic and IIc via a
t-Butoxycarbonyl Protected Aminooctanol
Intermediate
5'-Deoxy-5'-chloro-2',3'-isopropylideneadenosine (IIIb)

A 19.3 g (19.5 mL, 162 mmol) amount of thionyl chloride was added dropwise to 150 ml of ice-cold dry hexamethylphosphoric triamide (HMPA) under a nitrogen atmosphere. To the resulting cooled solution was added 18.6 g (60 mmol) of 2',3'-isopropylideneadenosine in portions. When the adenosine was added the color of the solution changed immediately from pale yellow to orange and then reddish. After 5 hr. stirring at ambient temperature, the reaction mixture was poured into a well-stirred mixture of ice-water (900 g), and the reaction flask was rinsed with water. The aqueous solution thus obtained was adjusted to pH=9 with conc. NH$_4$OH to give a white precipitate. The precipitate was collected and redissolved in chloroform. The chloroform solution was decolorized with charcoal to give a pale yellow solution, which was then poured into petroleum ether to give 17.2 g (88%) of white precipitate with mp 278° C. (dec.). This material was shown to be homogeneous on TLC [Silica, EtOAc:CHC$_3$ (9:1)] and HPLC (50% aqueous methanol, ODS-1). NMR(CDCl$_3$): $\delta$1.4 (3H, s), $\delta$1.6 (3H, s), $\delta$3.7 (2H, dd, H$_{5'}$, J=6 Hz, J=5 Hz), $\delta$4.46 (1H, dt, H$_{4'}$, J=2 Hz), $\delta$5.11 (1H, dd, H$_{3'}$, J=2 Hz, J=7 Hz), $\delta$5.48 (1H, dd, H$_{2'}$, J=2 Hz, J=7 Hz), $\delta$6.1 (1H, d, H$_{1'}$, J=2 Hz), $\delta$6.6 (2H, broad singlet, —NH$_2$), $\delta$7.86 (1H, s, H$_2$), $\delta$8.25 (1H, s, H$_8$).

Anal: C$_{13}$H$_{16}$ClN$_5$O$_3$ (C, H, N).

5'-Deoxy-5'-chloro-N$^6$-formyl-2',3'-isopropylideneadenosine (IIIc)

A 2.22 g (6.8 mmol) amount of IIIb was dissolved in 20 ml of acetic-formic anhydride and 0.8 g (7.55 mmol) of anhydrous sodium carbonate was added. The resulting solution was allowed to stir at ambient temperature for 8 hr and the reaction was monitored by TLC [silica gel, EtOAc:CHCl$_3$ (9:1)]. At the beginning, CO$_2$ evolution occurred and a slightly cloudy solution was obtained, but this became clear at the end of the reaction. The mixture was then concentrated to almost dryness under reduced pressure and the residue was dissolved in 50 ml CHCl$_3$, which was then washed with H$_2$O (2×40 ml), saturated aq. NaHCO$_3$ (2×40 ml), and H$_2$O (40 ml) and dried over MgSO$_4$. After removal of the solvent 2.1 g (85%) of pure IIIc was obtained; mp 230° C. (dec.). NMR(DMSO-d$_6$): $\delta$1.28 (3H, s), $\delta$1.49 (3H, s), $\delta$3.82 (2H, d, H$_{5'}$, J=6 Hz), $\delta$4.41 (1H, dt, H$_{4'}$, J=2 Hz, J=6 Hz), $\delta$5.11 (1H, dd, H$_{3'}$, J=2 Hz, J=7 Hz), $\delta$5.54 (1H, dd, H$_{2'}$, J=7 Hz), $\delta$6.41 (1H, d, H$_{1'}$, J=2 Hz), $\delta$8.64 (1H, s, H$_2$), $\delta$8.67 (1H, s, H$_8$), $\delta$9.87 (1H, d,

J=9 Hz), $\delta$11.24 (1H, d, -C<u>H</u>O, J=1 Hz).

Anal: C$_{14}$H$_{16}$ClN$_5$O$_4$ (C, H, N).

5'-Deoxy-5'-thioacetyl-N$^6$-formyl-2',3'-isopropylideneadenosine IV

A 0.5 g (1.42 mmol) amount of IIIc, 0.485 g (4.26 mmol) of previously triturated potassium thioacetate and a catalytic amount of anhydrous LiI were dissolved in 35 ml of methyl ethyl ketone and the resulting solution was refluxed for 5 hr. After cooling, the dark brown solution was filtered with the aid of celite, and the filtrate was concentrated under reduced pressure with the bath temperature below 30° C. The residue thus obtained was taken into 40 ml chloroform and washed with H$_2$O (4×40 ml) and dried over MgSO$_4$. After the removal of the solvent, 280 mg of crude product was obtained which, after recrystallization from Et$_2$O:CHCl$_3$, gave 235 mg (42.1%) of pure 4 which exhibited spectral properties and mp identical to that of an authentic compound prepared by a previously published method.

3-Octanol

To a well-stirred solution of 19.2 g (0.15 mmol) of 3-octanone in 270 ml of 95% ethanol, cooled in an ice bath, was added in portions a solution of 3.9 g (0.103 mmol) of sodium borohydride in 27 ml of water. Ammonium hydroxide (15M, 27 ml) was added and the ice bath removed and stirring was continued in room temperature for 3 hr. The reaction mixture was concentrated to near dryness and the residue was partitioned between 250 ml each of CHCl$_3$ and H$_2$O. The organic layer was separated and the aqueous layer was extracted with CHCl$_3$ (2×200 ml). The combined extracts were washed with 5% HCl (350 ml), and saturated NaCl solution (350 ml) and dried over MgSO$_4$. After the removal of the solvent, the liquid residue was distilled under reduced pressure (bp 86°-87° C./24 Torr; lit. bp 69.5°-70.4° C./7 Torr (18)) to give 15.41 g (79.02%) of pure 3-octanol. NMR(CDCl$_3$): $\delta$0.93 (6H, t, CH$_3$), $\delta$1.37 (10H, broad multiplet, —CH$_2$—), $\delta$2.35 (1H, broad singlet, exchangeable with D$_2$O and shift to low field in pyridine, —OH), $\delta$3.47 (1H, m, >CHO—).

3-Bromooctane

To 8 ml (23 g, 85.3 mmol) of phosphorus tribromide was added dropwise 15 g (115.4 mmol) of 3-octanol over a ½ hr period. The resulting solution was heated at 100° C. (oil bath) for 2 hr, after which time the reaction mixture was cooled and poured into 200 ml ice-water which was extracted with CHCl$_3$ (3×120 ml). The combined organic extracts were washed with 5% Na$_2$S$_2$O$_3$ (2×200 ml), H$_2$O (200 ml), sat'd aq. NaHCO$_3$ (2×200 ml), H$_2$O (200 ml), and sat'd aq. NaCl (200 ml), and dried over MgSO$_4$. After the removal of the solvent under reduced pressure, the residue was distilled (bp 78°-80° C./18 Torr, lit. bp 84.4°-85.1° C./20 Torr (18)) to give 17.5 g (78.58%) of pure 3-bromooctane which exhibited C-Br band at 797 cm$^{-1}$ in the IR spectrum (18). NMR(CDCl$_3$): $\delta$1.0 (6H, t, CH$_3$), $\delta$1.31 (6H, broad singlet, —CH$_2$), $\delta$1.75 (4H, q,

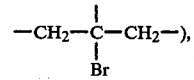

$\delta$3.90 (1H, m, >CHBr).

S-Adenosyl-3-methylthiooctane (IIb)

Route A: [From 5'-deoxy-5'-chloroadenosine IIIa] 3-Thioacetyloctane

To 6.2 g (54.3 mmol) of previously triturated potassium thioacetate in 60 ml of dry DMSO was added 7.0 g (36.27 mmol) of 3-bromooctane and the resulting solution was stirred overnight at ambient temperature. The reaction mixture was then poured into 500 ml of H$_2$O and extracted with chloroform (2×250 ml). The combined CHCl$_3$ extracts were washed with H$_2$O (2×250 ml), and sat'd aq. NaCl (250 ml) and dried over MgSO$_4$. After removal of the solvent, 6.8 g (100%) of crude product residue was distilled (bp 94°-95° C./22 Torr) to give 6.1 g (89.7%) of pure product NMR(CDCl$_3$): $\delta$0.67-1.10 (6H, m, CH$_3$), $\delta$1.10-1.97 (10H, m, —CH$_2$—), $\delta$2.3 (3H, s, CH$_3$—C=), $\delta$3.48 (1H, quintet, >CH—S—). Ir (thin film, cm$^{-1}$): 1689 ($\geq$C=O).

Anal: $C_{10}H_{20}OS$ (C, H, S).

S-adenosyl-3-thiooctane (Ib)

A 480 mg (2.55 mmol) amount of 3-thioacetyloctane in 10 ml of dry DMSO was degassed with a stream of nitrogen for 1 hr, after which time 485 mg (1.7 mmol) of 5'-deoxy-5'-chloroadenosine IIIa was added, followed by 2 ml of 4 M of NaOH. The resulting solution was stirred at ambient temperature overnight. The reaction mixture was then poured into 175 ml of H$_2$O to give a milky cloudy solution which was cooled at $-20°$ C. After warming to ca 25°, a solid was collected by filtration to give 600 mg (88.8%) of crude 5-adenosyl-3-thiooctane. The crude product was recrystallized from H$_2$O-MeOH to give 550 mg (81.4%) of pure 5-adenosyl-3-thiooctane Ib with mp 77°–80° C. NMR(MeOH-d$_4$): δ0.5–0.95 (6H, m, —CH$_3$), δ0.95–1.76 (10H, m, —CH$_2$—), δ2.48 (1H, quintet, >CH—S—), δ2.76 (2H, d, H$_{5'}$, J=6 Hz), δ3.9–4.37 (2H, m, H$_{3'}$ and H$_{4'}$), δ5.88 (1H, d, H$_{1'}$, J=5Hx), δ8.06 (1H, s, H$_2$), δ8.16 (1H, s, H$_8$). H$_{2'}$ peak obscured by OH signal (δ4.33–5.1) UV (λmax, nm): 219, 260, TLC: R$_1$ 0.93 on cellulose developed with BAW.

Anal: $C_{18}H_{29}N_5O_3S$ (C, H, N, S)

S-Adenosyl-3-methylthiooctane (IIb)

A 160 mg. (0.4 mmol) amount of 5-adenosyl-3-thiooctane Ib was methylated in 1.5 ml of 88% formic acid with 0.5 ml of methyl iodide. The resulting solution was stirred at ambient temperature, protected from the light, for 3 days, after which time the reaction mixture was partitioned between 50 ml each of ether and H$_2$O. The aqueous layer was separated, washed with ether (3×50 ml) and lyophilized to give 150 mg (61.9%) of the iodide salt. NMR(D$_2$O): δ0.6–1.5 (12, broad complex, —CH$_3$ and —CH$_2$—), δ1.5–2.05 (4H, broad complex,

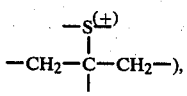

δ3.66 (1H, m,

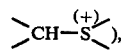

δ3.66–4.03 (2H, broad,

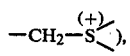

δ6.15 (1H, d, H$_{1'}$), δ8.25 (1H, s, H$_2$), δ8.33 (1H, s, H$_8$). H$_{2'}$, H$_{3'}$ and H$_{4'}$ peaks obscured by H$_2$O signal (δ4.50–5.4). The iodide was converted to a perchlorate salt by ion-exchange on a AG-X8 column, to give pure 5-adenosyl-3-methylthiooctane (IIb) as a white solid after lyophilization. The slightly hydroscopic product has mp 78°–80° C. UV (λmax, nm): 216, 259. TLC: R$_f$ 0.7 and 0.84 on cellulose developed with 5% aqueous Na$_2$HPO$_4$ and BAW (12:3:5), respectively.

Anal: $C_{19}H_{32}H_5O_3S \cdot ClO_4$ (C, H, N, S, Cl)

Preparation of 5-Adenosyl-1,8-Diamino-3-(methylthio)octane(IIc)

1,8-Dichloro-3-octanol a. 6-chlorohexanoyl chloride: A 2.26 g (16.6 mmol) amount of zinc chloride was added to 77.3 g (667 mmol) of ε-caprolactone in an ice bath to give a reddish solution to which 94.0 g (790 mmol) of thionyl chloride was added dropwise. After addition, the color of the reaction mixture was a dark brown which gradually became lighter in color as the reaction mixture was heated at 50°–60° C. overnight. NMR spectra indicted that all the starting lactone had been consumed by this time. After the removal of the excess of thionyl chloride under reduced pressure, the crude product was vacuum distilled (bp 70°–72° C./1.5 Torr) to give 57.49 g (51%) of a clear, colorless liquid. NMR (CDCl$_3$): δ1.63 (6H, m, —CH$_2$—), δ2.88 (2H, t,

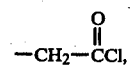

J=3.5 H$_z$), δ3.57 (2H, t,

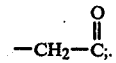

J=3.0 H$_z$). IR (thin film, cm$^{-1}$): 1798 (>C=O).

Anal: $C_6H_{10}Cl_2O$ (C, H).

b. 1,8 dichloro-3-octanone: A well stirred, ice-cooled solution of 30.35 g (179.6 mmol) of 6-chlorohexanoyl chloride in 300 ml of dry CCl$_4$ was degassed with nitrogen for ½ hr. AlCl$_3$ (26.34 g, 179.6 mmol) was added in portions, then ethylene was bubbled in at a rate so that no excess ethylene escaped from the reaction vessel. Ethylene was allowed to bubble through the reaction mixture at 0° C. for 2 hrs. and at ambient temperature overnight. The reaction mixture was poured into 800 ml ice-water and extracted with chloroform (2×400 ml). The combined chloroform extracted were washed with sat'd aq. NaHCO$_3$ (500 ml), H$_2$O (500 ml), sat'd NaCl (500 ml) and dried over MgSO$_4$. After the removal of the solvent, 15.2 g (43%) of crude 1,8-dichlorooctanone was obtained, which was used without further purification. NMR(CDCl$_3$): δ1.44 (6H, m, —CH$_2$—), δ2.34 (2H, t,

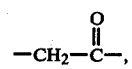

J=3.0 Hz), δ2.85 (2H, t,

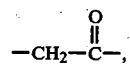

J=3.0 Hz), δ3.52 (2H, t, —CH$_2$Cl, J=3 Hz) δ3.74 (2H, t, —CH$_2$Cl, J=3.0 Hz).

c. 1,8-dichloro-3-octanol: To a well-stirred solution of 15.08 g (77 mmol) of 1,5-dichloro-3-octanone in 15 ml of 95% ethanol, cooled in an ice bath, was added a solution of 1.97 g (52 mmol) of sodium borohydride in 7 ml H$_2$O. 20 ml of concentrated NH$_4$OH was added and the resulting solution was stirred at ambient temperature for 1 hr. after the ice bath was removed. The reaction mixture was poured into 350 ml of H₂O and extracted with CHCl₃ (2×350 ml). The combined extracts were washed with 5% HCl solution (300 ml) and dried over MgSO₄. After removal of the solvent under reduced pressure, the residue was vacuum distilled (bp 95°–97° C.-C/0.3 Torr) to give 10.49 g (69%) of pure product NMR(CDCl₃): δ1.42 (6H, broad complex multiplet, —CH₂—), δ1.85 (4H, m, -C$\underline{H}$₂-C(OH)—C$\underline{H}$₂—), δ2.24 (1H, broad singlet, —OH, exchangable), δ3.33–3.9 (5H, overlapped multiplet, —CH₂Cl and >CHO—). IR (thin film, cm⁻¹): 3356 (—OH).

Anal: C₈H₁₆Cl₂O (C, H, Cl).

N,N,N',N'-tetra-t-butoxycarbonyl-3-hydroxyl-1,8-octanediamine 1.2 g of 57% of sodium hydride in wax was washed three times with dry benzene, the benzene removed by decantation, and the residual NaH decanted dried at high vacuum to remove the last traces of solvent; yield 820 mg (34 mmol) of sodium hydride. To a suspension of this 820 mg (34 mmol) of sodium hydride in 40 ml of dry DMF was added 6.2 g (28.3 mmol) of di-t-butyl iminodicarboxylate. After vigorous stirring overnight at 60° C., a catalytic amount of lithium iodide was added, followed by 2.34 g (14.1 mmol) of 1,8-dichloro-3-octanol and the resulting solution was heated at 60° continuously for another 3 days. The reaction mixture was cooled, diluted with 400 ml of H₂O, and extracted with CHCl₃ (2×400 ml). The combined chloroform extracts were washed with H₂O (3×200 ml), sat'd aq. NaCl solution (2×200 ml), and dried over MgSO. After removal of the solvent under reduced pressure and drying under high vacuum, 6.94 g (87.6%) of N,N,N'N'-tetra-t-butoxycarbonyl-3-hydroxyl-1,8-octanediamine was obtained as a chromatographically pure oil. NMR(CDCl₃): δ1.09–2.1 (46H, complex, —CH₂— and —CH₃), δ3.56 (4H, m, —CH₂N<), δ4.96 (1H, m, >CHO-). For further characterization, this produce was converted to 1,8-diamino-3-octanol by treatment with CF₃COOH. TLC: R$_f$ on silica gel, n-propanol:NH₃:H₂O (6:8:1), and MNR were identical with those of 1,8-diamino-3-octanol prepared by an independent route.

N,N,N',N'-tetra-t-butoxycarbonyl-3-tosyloxy-1,8-octanediamine

To a solution of 5.22 g (9.3 mmol) of N,N,N',N'-tetra-t-butoxycarbonyl-3-hydroxy-1,8-octanediamine in 27 ml dry pyridine, cooled in an ice bath, was added 7.9 g (41.4 mmol) of recrystallized tosyl chloride in portions and the resulting solution was stirred at 4° C. for 3 days. The reaction mixture was then poured into 500 ml of ice water and extracted with ether (3×270 ml). The combined ether extracts were washed with 5% cupric chloride solution to remove pyridine, sat'd aq. NaCl solution (3×200 ml), and dried over MgSO₄. After the removal of the solvent under reduced pressure and drying at high vacuum, 5.29 g (79.5%) of N,N,N',N'-tetra-t-butoxycarbonyl-3-hydroxy-1,8-octanediamine was obtained as an oil. TLC: R$_f$ 0.77 on silica gel, EtOAc:CHCl₃ (1:4), NMR (CDCl₃): δ1.03–2.13 (46H, complex, —CH₂— and —CH₃), δ2.46 (3H, s, —CH₃), δ3.50 (4H, m, —CH₂N<), δ4.73 (1H, m, >CHO-), δ7.23–7.96 (4H, AA'BB', aromatic).

N,N,N',N'-tetra-t-butoxycarbonyl-3-bromo-1,8-octanediamine

A 2.68 g (3.74 mmol) amount of N,N,N',N'-tetra-t-butoxycarbonyl-3-tosyloxy-1,8-octanediamine in 20 ml dry DMSO was treated with 1.6 g (18.4 mmol) of previously dried lithium bromide and the resulting solution was stirred at ambient temperature for 3 days. The reaction mixture was then poured into 200 ml of CHCl₃, washed with H₂O (2×140 ml), sat'd aq. NaCl solution (2×140 ml), and dried over MgSO₄. After removal of the solvent under reduced pressure and drying under high vacuum, 2.24 g (95.8%) of N,N,N',N'-tetra-t-butoxycarbonyl-3-bromooctane was obtained as a very viscous oil. NMR(CDCl₃): δ1.13–2.06 (4H, complex, —CH₂— and —CH₃), δ3.45 (4H, m, -CH₂N<), δ4.66 (1H, m >CHBr). IR(thin film, cm⁻¹): 1730 (C=O)

N,N,N',N'-tetra-t-butoxycarbonyl-S-(2',3'-isopropylideneadenosyl)-1,8-diamino-3-thiooctane A 59 mg (1.09 mmol) amount of sodium methoxide in 11 ml dry methanol was degassed with a stream of nitrogen for 1 hr at ambient temperature, and 271 mg (0.688 mmol) of 5'-thioacetyl-5'-deoxy-N⁶-formyl-2',3'-isopropylideneadenosine was added. The reaction (the generation of the free thio compound in solution) was monitored by TLC (silica gel, EtOAc). After 10 min., 420 mg (0.688 mmol) of N,N,N',N'-tetra-t-butoxycarbonyl-3-bromo-1,8-octanediamine was added, and a new compound (R$_f$0.38) was formed after 2 hr. as shown by TLC. After continuously stirring at ambient temperature overnight, the solvent was removed to near dryness under reduced pressure, and the residue was partitioned between 150 ml of CHCl₃ and 100 ml of H₂O. The organic layer was separated, washed with H₂O (2×100 ml), sat'd NaCl solution (100 ml), and dried over MgSO₄. After removal of the solvent under reduced pressure, the crude product (450 mg) was purified on preparative silica gel plate developed with EtOAc and the band at R$_f$ 0.38 was removed and the desired product eluted with MeOH:CHCl₃ (1:1; 4×100 ml). The combined eluents were concentrated to near dryness, the residue was re-dissolved into CHCl₃, and filtered. The filtrate was concentrated and dried under high vacuum to give 100 mg (16.8%) of pure thioether as a solid. NMR(CDCl₃): δ1.03–2.26 (52H, complex, —CH₂ and —CH₃), δ2.76 (2H, d, H$_{5'}$, J=6 Hz), δ3.03 (1H, m, >CH-S-), δ3.60 (4H, m, —CH₂-N<), δ4.4 (1H, m, H$_{4'}$), δ5.03 (1H, m, H$_{3'}$), δ5.46 (1H, m, H$_{2'}$), δ5.86 (1H, s, H$_{1'}$), δ6.01 (2H, s, —NH₂), δ7.83 (1H, s, H₂), δ8.25 (1H, s, H₈)

S-Adenosyl-1,8-diamino-3-(methylthio)octane (IIc)

A 84 mg (97 mmol) amount of N,N,N',N'-tetra-t-butoxycarbonyl-S-(2',3'-isopropylideneadenosyl)-3-thi-octyl-1,8-diamine in 2 ml of 88% formic acid was treated with 100 µL (228 mg, 1.6 mmol) of methyl iodide. The resulting solution, protected from light was continuously stirred at ambient temperature for 3 days. The reaction was monitored by TLC (silica gel, EtOAc) which showed that a sulfonium salt (R$_f$0.0) was formed, and the starting thioether was consumed after 1 day. The reaction mixture was then poured into H₂O (50 ml) and extracted with ether (3×50 ml). The aqueous layer was separated and lyophilized to give the sulfonium iodide. NMR (D₂O): δ1.06–1.76 (6H, broad complex, —CH₂—), δ1.76–2.36 (4H, broad complex,

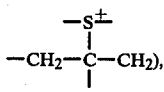

δ2.93 (3H, s,

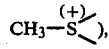

δ3.23-3.9 (5H, m, -CH₂N< and

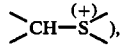

δ3.9-4.06 (2H, broad,

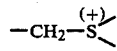

,H₅'), δ8.36 (2H, s, H₂ and H₈). The peaks for H₂', H₃' and H₄' were obscured by the HOD signal (δ4.0-5.4). The iodide thus obtained was exchanged to the perchlorate salt by use of an AGl-X8 column to give 26 mg (40%) of pure product as a white solid, which was very hygroscopic. UV(λmax, nm): 211, 260. TLC: R_f 0.74 cellulose, 5% aqueous Na₂HPO₄.

S-Adenosyl-1,8-diamino-3-thiooctane (Ic) can be prepared by hydrolysis of the ketal: N,N,N',N'-tetra-t-butoxycarbonyl-S-(2',3'-isopropylideneadenosyl)-3-thiooctyl-1,8-diamine in acid solution as described above.

Dimethyl-(5'-adenosyl)sulfonium perchlorate 120 mg (4 mmol) of 5'-methylthioadenosine (Ia), prepared according to the method published by Coward et al, (J. Med. Chem. 20, 500 (1977), was methylated to give 140 mg (84.1%) of product by the method described previously for S-adenosyl-3-methyl-thiooctane (IIa) with mp 76° C. (dec.). NMR(D₂O): δ2.96 (6H, s, —S(CH₃)₂), δ3.85 (2H, d, H₅', J=6 Hz), δ4.45-4.75 (2H, complex, H₃' and H₄'), δ4.8-5.08 (1H, m, H₂'), δ6.08 (1H, d, H₁', J=5 Hz), δ8.21 (1H, s, H₂), δ8.26 (1H, s, H₈). UV (λmax, nm): 207,259.

Preparation of S-Adenosyl-1,8-Diamino-3-thiooctane(Ic) via Azide Intermediates

1,8-Diazido-3-hydroxyoctane

A mixture of 5.5 g (27.6 mmol) of 1,8-dichloro-3-octanol, 5.5 g (84.57 mmol) of sodium azide, and a catalytical amount of anhydrous lithium iodide in 25 ml of dry DMF was heated to 60° C.±5° C. (oil bath) for 1 day, and then stirred at ambient temperature for another day. The solvent was then removed to near dryness under vacuum, at a temperature of ca. 30° C. The residue was then partitioned between 250 ml each of CHCl₃ and H₂O. The organic layer was separated and washed with H₂O (2×250 ml), sat'd aq. NaCl (250 ml), and dried over MgSO₄. After removal of the solvent, the crude product was distilled (bp 105°-106° C./0.015 Torr) to give 5.25 g (89.7%) of pure 1,8-diazido-3-hydroxyoctane. NMR(CDCl₃): δ1.18-2.0 (10H, complex, —CH₂—), δ2.43 (1H, broad singlet, —OH), δ3.08-4.01 (5H, complex and CHO— and —CH₂N₃). IR(thin film, cm⁻¹): 3448(OH), 2105(-N₃).

Anal: C₈H₁₆N₆O.

1,8-Diazido-3-tosyloxyoctane

A 4.24 g (20 mmol) amount of 1,8-diazido-3-hydroxyoctane in 40 ml of dry pyridine was cooled in an ice bath; 16.9 g (88.89 mmol) of recrystallized tosyl chloride was added in portions and the resulting solution was stirred at 4° for 1 day. A white precipitate, presumably pyridinium hydrochloride, was formed from a clear pink solution after several hours. The reaction mixture was poured into 750 ml of ice water and extracted with CHCl₃ (3×250 ml). The combined CHCl₃ extracts were washed with H₂O (2×250 ml), cold 5% H₂SO₄ (2×250 ml), sat'd aq. NaHCO₃ (250 ml) and sat'd aq. NaCl (250 ml) and dried over MgSO₄. After removal of the solvent and drying under high vacuum, 9.92 g (100%) of the crude product 1,8-diazido-3-tosyloxyoctane was obtained and used without any further purification. NMR(CDCl₃): δ1.0-2.2 (10H, complex, —CH₂—), δ2.47 (3H, s, —CH₃), δ3.03-3.66 (4H, m, —CH₂N₃), δ4.68 (1H, quintet, >CH-O-), δ7.23-7.98 (4H, AA'BB', aromatic). IR(thin film, cm⁻¹): 2109 (-N₃).

1,8-Diazido-3-S-thioacetyloctane

A 3.43 g (30 mmol) amount of previously triturated potassium thioacetate was added to a solution of 9.92 g (20 mmol) of crude 1,8-diazido-3-tosyloxyoctane in 90 ml of dry DMSO, and the resulting solution was stirred at ambient temperature for 1 day. The reaction mixture was then poured into 500 ml of H₂O and extracted with CHCl₃ (3×200 ml). The combined CHCl₃ extracts were washed with H₂O (4×300 ml), sat'd aq. NaCl (2×300 ml) and dried over MgSO₄. After removal of the solvent and drying under high vacuum, 4.33 g (80.2%) of crude product was obtained. Vacuum distillation (bp 138°-141° C./0.25 Torr) gave 2.1 g (39%) of the pure NMR(CDCl₃): δ1.16-2.13 (10H, complex, —CH₂—), δ2.36 (3H, s, $$\underset{\|}{\overset{O}{-C}}-CH_3),$$

δ3.1-3.9 (5H, complex, >CHS-, —CH₂N₃). IR(thin film, cm⁻¹): 2105 (-N₃), 1687 (>C=O). R_f 0.82 on silica gel, MeOH-CHCl₃ (1:4).

Anal: C₁₀H₁₈N₆O.

S-Adenosyl-1,8-diazido-3-thiooctane

A 688 mg (2.55 mmol) amount of pure 1,8-diazido-3-S-thioacetyloctane was coupled with 5'-deoxy-5'-chloroadenosine by the procedure described previously to give 541 mg (66.7%) of practically pure S-adenosyl-1,8-diazido-3-thiooctane which was recrystallized from H₂O-MeOH to give the pure compound with a mp 44°-46° C. TLC: R_f 0.71, silica gel, MeOH-CHCl₃ (1:4); HPLC: t_r 21.3 min., ODS-2, 65% aq. MeOH. NMR(MeOH-d₄): δ0.83-1.9 (10H, complex, —CH₂—), δ2.26-2.63 (1H, m; >CH-S-), δ2.63-2.9 (2H, d H₅', J=6 Hz), δ2.9-3.53 (4H, m, -CH₂N₃), δ3.83-4.4 (2H, complex, H₃, and H₄'), δ5.91 (1H, d, H₁', J=5 Hz), δ8.1 (1H, s, H₂). δ8.16 (1H, s, H₈). H₂' peak obscured by OH signal (δ4.36-4.85). Ir (Nujol, cm⁻¹): 2118 (N₃). UV(-λmax, nm): 210, 259. TLC: R_f 0.71, silica gel; CHCl₃-MeOH (4:1), and R_f 0.88, cellulose, BAW.

Anal: $C_{18}H_{27}N_{11}O_3S$.

S-Adenosyl-1,8-diamino-3-thiooctane (Ic)

A 280 mg (0.49 mmol) amount of S-adenosyl-1,8-diazido-3-thiooctane and 420 mg (1.6 mmol) of triphenylphosphine were dissolved in 1 ml of dry pyridine and the resulting solution was kept at ambient temperature with stirring for 1 hr, during which time, gas evolution (presumably $N_2$) was observed. Ammonium hydroxide (13 M, 300 μl) was then added and stirring was continued for another 2 hrs. The excess ammonium hydroxide and pyridine were removed under high vacuum at room temperature and the resulting residue was dissolved in 70 ml of $H_2O$. The aqueous solution was washed with benzene (3×50 ml) and ether (3×50 ml), and then lyophilized to give 212 mg (82.5%) of free aminonucleoside as a hygroscopic white solid. NMR($D_2O$): δ0.67–1.96 (10H, broad, —$CH_2$—), δ2.3–3.06 (7H, complex, —$CH_2N$, >CHS- and $H_{5'}$), δ4.06–4.4 (2H, complex, $H_3$, and $H_{4'}$), δ5.91 (1H, d, $H_{1''}$, J=5 Hz), δ8.03 (1H, s, $H_2$), δ8.16 (1H, s, $H_8$). The peak of $H_2$, was obscured by the HOD signal (δ4.43–5.06). UV(λmax, nm): 212, 259. TLC: $R_f$ 0.18 and 0.57 developed with BAW on silica gel and cellulose plate respectively, as well as $R_f$ 0.71 on cellulose with 5% $Na_2HPO_4$. Anal: $C_{18}H_{31}N_7O_3S$ (C, H, N).

Having now fully described this invention, it will be apparent to one of ordinary skill in the art that many changes and modifications can be made thereto without departing from the spirit or scope of the invention as set forth herein.

What is claimed as new and desired to be secured by letters patent of the United States is:

1. A compound having the formula:

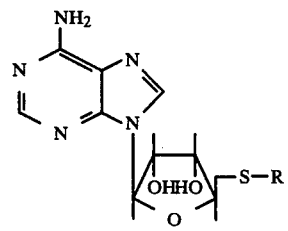

wherein R is

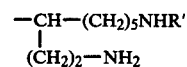

wherein R' is hydrogen or aminopropyl and salts thereof.

2. A pharmaceutical composition useful in the treatment of cystic fibrosis or a parasitic infection, comprising:
    a pharmaceutically effective amount of the compound of claim 1 in a mixture with a pharmaceutically acceptable carrier.

3. A method of treating a subject having cystic fibrosis, comprising:
    administering to said subject a pharmaceutically effective amount of a pharmaceutical composition containing the compound of claim 1.

4. A method of treating a subject having a parasitic infection, comprising:
    administering to said subject a pharmaceutically effective amount of a pharmaceutical composition containing the compound of claim 1.

* * * * *